United States Patent [19]

Jojima et al.

[11] Patent Number: 4,738,961

[45] Date of Patent: Apr. 19, 1988

[54] PYRIDAZINONE DERIVATIVES, THEIR PREPARATION AND THEIR USE IN AGRICULTURAL COMPOSITIONS AND THE TREATMENT OF SEED AND PLANTS

[75] Inventors: Teruomi Jojima; Hideo Takeshiba; Takashi Matsui, all of Hiromachi; Yukiyoshi Takahi, Shiga, all of Japan

[73] Assignee: Sankyo Company, Limited, Tokyo, Japan

[21] Appl. No.: 404,870

[22] Filed: Aug. 3, 1982

[30] Foreign Application Priority Data

Aug. 10, 1981 [JP] Japan .................. 56-124974

[51] Int. Cl.$^4$ .................. C07D 237/14; C07D 265/30
[52] U.S. Cl. .................. 514/227; 544/238; 544/239; 544/336; 544/406; 514/252; 514/253; 514/255
[58] Field of Search .................. 544/336, 238, 239; 424/250 F; 514/252, 253, 227

[56] References Cited

U.S. PATENT DOCUMENTS

| | | | |
|---|---|---|---|
| 2,624,730 | 1/1953 | Steck | 544/239 |
| 2,712,542 | 7/1955 | King et al. | 544/239 |
| 2,938,902 | 5/1960 | DuBreuil | 544/239 |
| 3,883,530 | 5/1975 | Bublitz | 544/224 |
| 4,052,395 | 10/1977 | Sojima et al. | 544/239 |

FOREIGN PATENT DOCUMENTS

| | | | |
|---|---|---|---|
| 2006020 | 9/1971 | Fed. Rep. of Germany | 544/336 |
| 2445681 | 4/1976 | Fed. Rep. of Germany | 544/239 |
| 2990 | 2/1969 | Japan | 544/239 |
| 13713 | 6/1969 | Japan | 544/239 |
| 1043776 | 4/1976 | Japan | 544/239 |
| 5118470 | 9/1980 | Japan | 424/250 |
| 6113767 | 9/1981 | Japan | 424/250 |
| 6156206 | 12/1981 | Japan | 424/250 |
| 467728 | 3/1978 | Spain . | |
| 1533010 | 11/1978 | United Kingdom . | |
| 2047702 | 12/1980 | United Kingdom . | |

OTHER PUBLICATIONS

Noller, Carl, Textbook of Organic Chemistry, W. B. Saunders, Philadelphia, (1966), pp. 100, 101, 128, 129, 196.
Rufenacht, Kurt; Helretica Chim. Acta: vol. 56, (1973), pp. 2186–2204.

Primary Examiner—Donald G. Daus
Assistant Examiner—Brian Leslie
Attorney, Agent, or Firm—Frishauf, Holtz, Goodman & Woodward

[57] ABSTRACT

Compounds of formula (I):

[in which:
A represents a group of formula —CH=CH— or —CH$_2$—CH$_2$—;
R$^1$ represents a halogen atom;
R$^2$ represents a hydrogen atom, a hydroxy group, a halogen atom, an alkyl group or an alkoxy group;
R$^3$ represents a hydrogen atom or a halogen atom; and
Y represents a hydroxy group, a halogen atom, an alkylamino group, a dialkylamino group, an alkenylamino group, a dialkenylamino group, an anilino group (in which the aromatic ring is unsubstituted or has one or two substituents selected from halogen atoms and alkyl groups), a cycloalkylamino group, a 1-pyrrolidinyl group, a piperidino group, a morpholino group, a group of formula (in which R$^4$ represents an alkyl group or a phenyl group) or a group of formula (in which A, R$^1$, R$^2$ and R$^3$ are as defined above)] are useful agricultural fungicides having greater systemic activity and chemical stability than known compounds of similar structure. They may be applied as such or in a conventional preparation to seeds and growing plants. They may be prepared by reacting a 6-(substituted phenyl)-3(2H)-pyridazinone with formaldehyde and optionally with a halogenating agent, an appropriate amine or piperazine.

24 Claims, No Drawings

PYRIDAZINONE DERIVATIVES, THEIR PREPARATION AND THEIR USE IN AGRICULTURAL COMPOSITIONS AND THE TREATMENT OF SEED AND PLANTS

BACKGROUND OF THE INVENTION

The present invention relates to a series of new pyridazinone derivatives which have fungicidal activity, and provides a method of preparing these compounds and agricultural fungicidal compositions containing them.

A number of pyridazinone derivatives is known to have fungicidal activity. For example, those disclosed in United Kingdom Patent Specification No. 1,533,010, which may be represented by the formula:

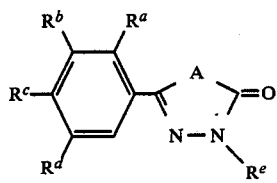

(in which $R^a$ may represent a hydrogen atom, a hydroxy group or an acyloxy group, $R^b$ and $R^d$ both represent halogen atoms or one represents a halogen atom and the other represents a hydrogen atom, $R^c$ represents, inter alia, a hydrogen or halogen atom or an alkyl or alkoxy group, and $R^e$ represents a hydrogen atom) have been found to be effective against a wide range of pathogenic fungi whilst not exhibiting any phytotoxicity, when employed at effective doses. Spanish Pat. No. 467,728 discloses processes for preparing some of the same compounds as are disclosed in United Kingdom Patent Specification No. 1,533,010 and also discloses a number of previously unknown, but related compounds, including some in which $R^e$ in the above formula represents an alkyl group.

Subsequently, United Kingdom Patent Specification No. 2,047,702A disclosed a series of compounds similar to those of the above formula but in which either the carbonyl group on the pyridazine ring has been replaced by a N-substituted carbamoyloxy group (or the sulphur analogue in which one or both of the oxygen atoms in the carbamoyloxy group has been replaced by a sulphur atom) or in which there is an alkyl-, aryl- or aralkyl-oxy (or thio) carbonyl group on the nitrogen atom adjacent the pyridazinone carbonyl group.

We have now discovered a series of compounds which are related to the prior art compounds described above but which are chemically more stable than those of United Kingdom Patent Specification No. 2,047,702A and which have greater systemic (i.e. penetrating) activity than do those of United Kingdom Patent Specification No. 1,533,010 and Spanish Pat. No. 467,728.

BRIEF SUMMARY OF INVENTION

The new pyridazinone derivatives of the present invention are those compounds which may be represented by formula (I):

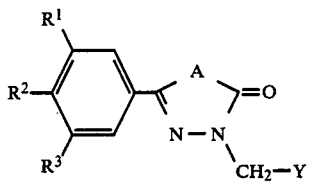

in which:
A represents a group of formula —CH=CH— or —CH$_2$—CH$_2$—;
$R^1$ represents a halogen atom;
$R^2$ represents a hydrogen atom, a hydroxy group, a halogen atom, an alkyl group or an alkoxy group;
$R^3$ represents a hydrogen atom or a halogen atom; and
Y represents a hydroxy group, a halogen atom, an alkylamino group, a dialkylamino group, an alkanylamino group, a dialkenylamino group, an anilino group (in which the aromatic ring is unsubstituted or has one or two substituents selected from halogen atoms and alkyl groups), a cycloalkylamino group, a 1-pyrrolidinyl group, a piperidino group, a morpholino group, a group of formula

(in which $R^4$ represents an alkyl group or a phenyl group) or a group of formula

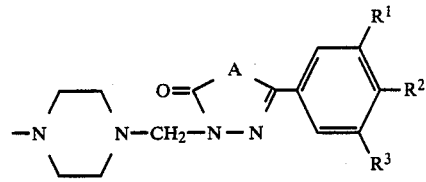

(in which A, $R^1$, $R^2$ and $R^3$ are as defined above).

The invention also provides a process for preparing the compounds of the invention in which a compound of formula (II): (in which A, $R^1$, $R^2$ and $R^3$ are as defined above) is reacted with formaldehyde to give a compound of formula (Ia):

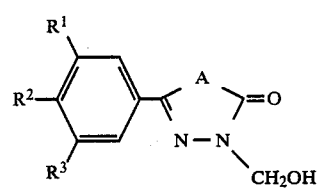

(in which A, $R^1$, $R^2$ and $R^3$ are as defined above) and, if necessary, this compound of formula (Ia) is reacted with a halogenating agent, an amine or piperazine, to give the desired compound of formula (I).

The invention still further provides an agricultural fungicidal composition comprising a fungicide in admixture with an agriculturally acceptable carrier or diluent, wherein the fungicide is at least one compound of formula (I).

The invention also provides a method of preventing or controlling fungal attack on seeds or growing plants by applying to the seeds or growing plants an effective amount of a fungicide, wherein the fungicide comprises at least one compound of formula (I).

DETAILED DESCRIPTION OF INVENTION

In the compounds of the invention, where $R^1$, $R^2$, $R^3$ or Y represents a halogen atom, this may be a chlorine, bromine, fluorine or iodine atom, but is preferably a chlorine or bromine atom.

Where $R^2$ or $R^4$ represents an alkyl group, The alkyl group is preferably a lower alkyl group, which may be a straight or branched chain alkyl group, and has from 1 to 4 carbon atoms, for example a methyl, ethyl, propyl, isopropyl, butyl or isobutyl group; of these, the methyl and ethyl, especially the methyl, groups are preferred.

Where $R^2$ represents an alkoxy group, this is preferably a lower alkoxy group, which may be a straight or branched chain group, and has from 1 to 4 carbon atoms. Examples of such groups include the methoxy, ethoxy, propoxy, isopropoxy, butoxy and isobutoxy groups, of which the methoxy and ethoxy, especially the methoxy, groups are preferred.

Where Y represents an alkylamino or dialkylamino group, the or each alkyl group may be a straight or branched chain group, and preferably has from 1 to 8 carbon atoms, for example, a methyl, ethyl, propyl, isopropyl, butyl, isobutyl, pentyl, hexyl, heptyl, octyl or 2-ethylhexyl group.

Where Y represents an alkenylamino or a dialkenylamino group, the or each alkenyl group is preferably a lower alkenyl group, which may be a straight or branched chain group, preferably having 3 or 4 carbon atoms. Examples of such groups include the allyl, 1-methyl-2-propenyl, 2-methyl-2-propenyl and 2-butenyl groups, of which the allyl group is preferred.

Where Y represents an anilino group having one or two substituents, the substituents may be halogen atoms (for example, chlorine, bromine, fluorine or iodine atoms) or alkyl groups, preferably lower alkyl groups (for example methyl, ethyl, propyl or isopropyl groups). Where there are two substituents, these may be the same or different, for example two halogen atoms, two alkyl groups or one halogen atom and one alkyl group.

Where Y represents a cycloalkylamino group, the cycloalkyl group is preferably a 5, 6 or 7 membered cycloalkyl group, for example a cyclohexyl, cyclopentyl or cycloheptyl group, of which the cyclohexyl group is preferred.

In general, the preferred compounds of formula (I) are those in which:
$R^1$ represents a halogen atom;
$R^2$ represents a hydrogen atom, a halogen atom or a lower alkyl group;
$R^3$ represents a hydrogen atom or a halogen atom; and
Y represents a halogen atom, a hydroxy group, an alkylamino group, dialkylamino group, a dialkenylamino group, a 1-pyrrolidinyl group, a piperidino group or a morpholino group.

The most preferred compounds are those in which:
$R^1$ and $R^3$ both represent halogen atoms and $R^2$ represents a lower alkyl group, particularly a methyl group, or a halogen atom; or
$R^1$ represents a halogen atom, $R^2$ represents a hydrogen atom or a halogen atom and $R^3$ represents a hydrogen atom; and Y represents a hydroxy group, a halogen atom, an alkylamino group, a dialkylamino group, a piperidino group or a morpholino group.

Especially preferred are those compounds in which:
$R^1$ and $R^3$ both represent chlorine atoms and $R^2$ represents a methyl group; or
$R^1$ represents a bromine atom and $R^2$ and $R^3$ both represent hydrogen atoms; or
$R^1$ and $R^2$ both represent chlorine atoms and $R^3$ represents a hydrogen atom.

We particularly prefer those compounds in which A represents a group of formula —CH=CH—.

The following is a list of representative examples of the pyridazinone derivatives of formula (I). The numbers appended to the compounds in this list are used hereinafter to identify the compounds.

1. 6-(3-Bromophenyl)-2-hydroxymethyl-3(2H)-pyridazinone.
2. 6-(3,5-Dichloro-4-methylphenyl)-2-hydroxymethyl-3(2H)-pyridazinone.
3. 6-(3,5-Dichloro-4-methylphenyl)-2-hydroxymethyl-4,5-dihydro-3(2H)-pyridazinone.
4. 6-(3-Bromophenyl)-2-hydroxymethyl-4,5-dihydro-3(2H)-pyridazinone.
5. 6-(3-Bromophenyl)-2-chloromethyl-3(2H)-pyridazinone.
6. 2-Chloromethyl-6-(3,4-dichlorophenyl)-3(2H)-pyridazinone.
7. 2-Chloromethyl-6-(3,5-dibromo-4-methylphenyl)-3(2H)-pyridazinone.
8. 2-Chloromethyl-6-(3,5-dichloro-4-methoxyphenyl)-3(2H)-pyridazinone.
9. 6-(3-Bromo-4-fluorophenyl)-2-chloromethyl-3(2H)-pyridazinone.
10. 6-(3,4-Dichlorophenyl)-2-N-isopropylaminomethyl-3(2H)-pyridazinone.
11. 6-(3,4-Dichlorophenyl)-2-N,N-dimethylaminomethyl-3(2H)-pyridazinone.
12. 6-(3-Bromophenyl)-2-N,N-dimethylaminomethyl-3(2H)-pyridazinone.
13. 6-(3-Bromophenyl)-2-(N-butyl-N-methylaminomethyl)-3(2H)-pyridazinone.
14. 2-(N-Allylaminomethyl)-6-(3,5-dichloro-4-hydroxyphenyl)-3(2H)-pyridazinone.
15. 6(3-Bromophenyl)-2-(N,N-diallylaminomethyl)-3(2H)-pyridazinone.
16. 2-Anilinomethyl-6-(3-chlorophenyl)-3(2H)-pyridazinone.
17. 2-(p-Chloroanilinomethyl)-6-(3,4-dichlorophenyl)-3(2H)-pyridazinone.
18. 6-(3,4-Dichlorophenyl)-2-(p-methylanilinomethyl)-3(2H)-pyridazinone.
19. 2-Cyclohexylaminomethyl-6-(3,4-dichlorophenyl)-3(2H)-pyridazinone.
20. 6-(3-Bromophenyl)-2-(1-pyrrolidinylmethyl)-3(2H)-pyridazinone.
21. 6-(3-Bromophenyl)-2-(1-pyrrolidinylmethyl)-4,5-dihydro-3(2H)-pyridazinone.
22. 6-(3-Bromophenyl)-2-piperidinomethyl-3(2H)-pyridazinone.
23. 6-(3,4-Dichlorophenyl)-2-piperidinomethyl-3(2H)-pyridazinone.
24. 6-(3-Bromo-4-fluorophenyl)-2-piperidinomethyl-3(2H)-pyridazinone.
25. 6-(3,4-Dichlorophenyl)-2-morpholinomethyl-3(2H)-pyridazinone.
26. 6-(3-Bromophenyl)-2-morpholinomethyl-3(2H)-pyridazinone.

27. 6-(3,5-Dichloro-4-methoxyphenyl)-2-morpholinomethyl-3(2H)-pyridazinone.
28. 6-(3,5-Dichloro-4-methylphenyl)-2-morpholinomethyl-3(2H)-pyridazinone.
29. 6-(3,5-Dichloro-4-methylphenyl)-2-morpholinomethyl-4,5-dihydro-3(2H)-pyridazinone.
30. 6-(3-Bromophenyl)-2-morpholinomethyl-4,5-dihydro-3(2H)-pyridazinone.
31. 6-(3-Chloro-4-methoxyphenyl)-2-(4-methyl-1-piperazinylmethyl)-3(2H)-pyridazinone.
32. 6-(3,5-Dichloro-4-methylphenyl)-2-(4-phenyl-1-piperazinylmethyl)-3(2H)-pyridazinone.
33. 1,4-Bis[6-(3-bromophenyl)-3(2H)-pyridazinon-2-ylmethyl]-piperazine.
34. 1,4-Bis[6-(3,4-dichlorophenyl)-3(2H)-pyridazinon-2-ylmethyl]-piperazine.
35. 6-(3,4-Dichlorophenyl)-2-hydroxymethyl-3(2H)-pyridazinone.

Especially preferred are Compounds No. 1, 2 and 35.

The compounds of formula (I) may be prepared by the following processes.

PROCESS 1

Compounds of formula (I) in which Y represents a hydroxy group, that is to say compounds of formula (Ia):

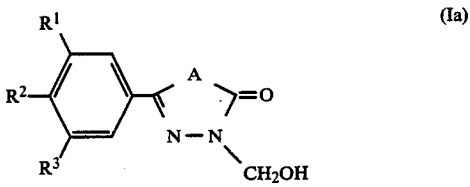

(in which A, $R^1$, $R^2$ and $R^3$ are as defined above) may be prepared by the reaction of a compound of formula (II):

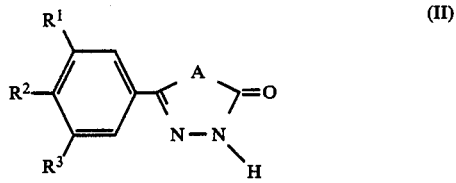

(in which A, $R^1$, $R^2$ and $R^3$ are as defined above) with formaldehyde. The formaldehyde is preferably employed in the form of an aqueous solution (such as that known as "formalin") or in the form of paraformaldehyde.

The amount of formaldehyde is preferably equimolar or greater with respect to the compound of formula (II).

The reaction is preferably carried out in the presence of a solvent, the nature of which is not critical, provided that it has no adverse effect upon the reaction. Examples of suitable solvents include alcohols (such as methanol, ethanol, isopropanol or butanol) and mixtures of one or more of these alcohols with water. The reaction is also preferably carried out in the presence of a small quantity of catalyst, which is preferably an inorganic base (such as sodium carbonate, sodium bicarbonate, potassium carbonate, sodium hydroxide, potassium hydroxide or calcium hydroxide) or a mineral acid (for example, sulphuric acid, hydrochloric acid or phosphoric acid).

The temperature at which the reaction is carried out is not critical and may vary over a wide range, however, we have found it is generally convenient to carry out the reaction at the reflux temperature of the solvent employed.

PROCESS 2

Compounds of formula (I) in which Y represents a halogen atom, that is to say compounds of formula (Ib):

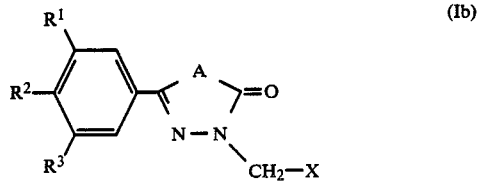

(in which A, $R^1$, $R^2$ and $R^3$ are as defined above and X represents a halogen atom) can easily be prepared by reacting a compound of formula (Ia), which may have been prepared by Process 1, as described above, with a halogenating agent.

Examples of suitable halogenating agents include thionyl chloride, thionyl bromide and phosphorus oxychloride. The amount of halogenating agent is preferably at least equimolar with respect to the compound of formula (Ia).

The reaction may be carried out in the presence or absence of a solvent. Where a solvent is employed, its nature is not critical, provided that it has no adverse effect on the reaction; suitable solvents include such aromatic hydrocarbons as benzene, toluene and xylene.

The halogenation reaction is preferably effected with heating, but the reaction temperature is not critical, and we therefore normally prefer to carry out the reaction at the reflux temperature of the solvent employed or of the reaction mixture.

It is also possible to prepare the compounds of formula (Ib) by reacting the compound of formula (II) directly with the halogenating agent and paraformaldehyde. In this case, the reaction is preferably carried out in the presence of a solvent (e.g. an aromatic hydrocarbon such as benzene, toluene or xylene) at a temperature from ambient to reflux. The amount of paraformaldehyde is preferably from 1 to 5 moles and that of halogenating agent is preferably from 1 to 10 moles, both per mole of compound (II).

PROCESS 3

Compounds of formula (I) in which Y represents the various substituted amine groups, that is to say compounds of formula (Ic):

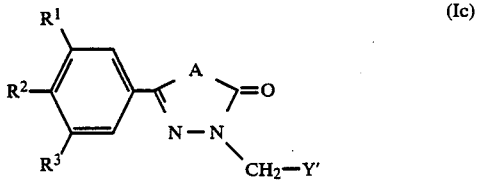

[in which A, $R^1$ $R^2$ and $R^3$ are as defined above and Y' represents an alkylamino group, a dialkylamino group, an alkenylamino group, a dialkenylamino group, an anilino group (whose aromatic ring may be unsubstituted or may have one or two halogen and/or alkyl substituents), a cycloalkylamino group, a 1-pyrrolidinyl group, a piperidino group, a morpholino group or a group of formula

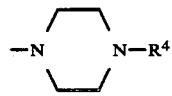

(in which $R^4$ is as defined above)] can easily be prepared by reacting a compound of formula (Ia) or (Ib), which may have been prepared by Processes 1 or 2, as described above, with an amine of formula HY' (in which Y' is as defined above).

This reaction is preferably effected in the presence of a solvent, the nature of which is not critical, provided that it has no adverse effect on the reaction. Examples of suitable solvents include: alcohols, such as methanol, ethanol, isopropanol or butanol; ethers, such as diethyl ether, diisopropyl ether, dioxane or tetrahydrofuran; aromatic hydrocarbons, such as benzene, toluene or xylene; ketones, such as acetone or methyl ethyl ketone; halogenated hydrocarbons, such as methylene chloride, ethylene chloride, chloroform or carbon tetrachloride.

The reaction temperature is not critical and may vary over a wide range; for convenience, we normally prefer to carry out the reaction at a temperature of from room temperature to the reflux temperature of the solvent employed.

The molar ratio of the compound of formula (Ia) or (Ib) to the amine HY' is preferably from 1:1 to 1:5, although, if the amine is a secondary amine, it may be employed in an amount greater 5 moles per mole of the compound of formula (Ia) or (Ib).

Where the compound of formula (Ib) is employed, the reaction is preferably effected in the presence of an acid-binding agent, for example an inorganic base (such as sodium carbonate, potassium carbonate or sodium bicarbonate) or an organic base (such as pyridine or triethylamine).

Alternatively, compounds of formula (Ic) can be prepared by heating the compound of formula (II) with formaldehyde (preferably in the form of formalin or paraformaldehyde) and the amine of formula HY' in the presence of a solvent. The solvents and amounts of reagents may be chosen from those suggested when the reactions are carried out separately. The reaction temperature may range from ambient to reflux temperature.

PROCESS 4

Those compounds of formula (I) in which Y represents a group of formula

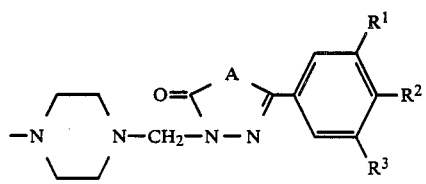

that is to say compounds of formula (Id):

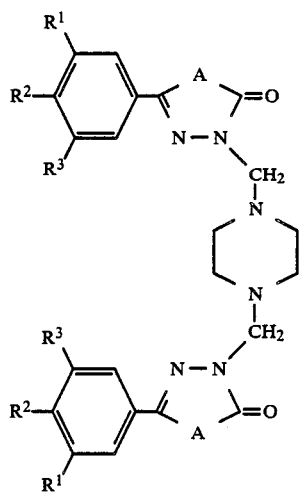

(in which A, $R^1$, $R^2$ and $R^3$ are as defined above), can easily be prepared by heating a compound of formula (II) with formaldehyde (preferably in the form of formalin or paraformaldehyde) and piperazine under the same reaction conditions as are described in the aforementioned Process 3.

The molar ratio of compound (II), formaldehyde and piperazine is preferably 2:2:1.

After completion of any of the reactions described in the above Processes 1, 2, 3 and 4, the desired products may be isolated by conventional means and, if necessary, further purified, for example, by recrystallisation and/or chromatography, particularly column chromatography.

The compounds of the present invention may be employed as agricultural fungicides and show a preventive and curative effect against plant diseases, without damaging the host plants. They have better systemic action (i.e. penetration of the compounds into and translocation of the compounds in the plant body) than do the compounds of United Kingdom Patent Specification No. 1,553,010 and Spanish Patent Specification No. 467,728, and have greater chemical stability than do the compounds of United Kingdom Patent Specification No. 2,047,702A.

Specifically, they are particularly effective in the control of sheath blight, which is a very serious disease attacking rice plants; for this purpose, they are preferably employed in the form of a spray, particularly a foliar spray, or are applied, dissolved or dispersed in water, to the soil surface. They also effectively control damping-off of various crops, such as beet, cotton plants and plants of the gourd family, which disease is caused by pathogenic fungi of the class Rhizoctonia. They are also effective in the control of infectious soil-borne diseases, for example southern blight (which attacks the egg-plant and plants of the gourd family) and black scurf (which attacks potatoes); in this case, they are preferably employed in the form of a soil fungicide or a seed disinfectant.

At effective doses, the compounds of the invention do not exhibit any phytotoxicity to such plants as rice plants, tomato plants, potatoes, cotton plants, egg-plants, cucumbers and kidney beans. Moreover, they may be used effectively as fungicides in orchards, non-crop land and forests.

The compounds of the invention may be formulated as preparations of the type commonly employed as agricultural fungicides, for example powdery dusts, coarse dusts, fine granules, coarse granules, wettable powders, emulsifiable concentrates, aqueous liquids, water-soluble powders and oil suspensions, by mixing them with a carrier and, if required, with other auxiliary agents. The carrier employed may be natural or synthetic and organic or inorganic; it is mixed with the active compound to assist that compound to reach the material to be treated and to make it easier to store, transport or handle the active compound.

Suitable solid carriers are: inorganic substances, such as clays (examples of which are kaolinite, montmorillonite or attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; or urea.

Examples of suitable liquid carriers are: paraffinic or naphthenic hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers, such as dioxane and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; polar solvents, such as dimethylformamide and dimethyl sulphoxide; and water.

The fungicidal compositions of the present invention may contain surface active agents to emulsify, disperse, wet, spread, bind, control disintegration of, improve fluidity of or rust-proof the fungicidal composition or to stabilize the active compound; although any of the conventional classes of surface active agent, be they non-ionic, anionic, cationic or amphoteric, may be employed, we prefer to employ non-ionic and/or anionic surface active agents. Examples of suitable non-ionic surface active agents are: the polymerization adducts of ethylene oxide with higher alcohols, such as lauryl alcohol, stearyl alcohol or oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan, and said fatty acid esters themselves; and the polymerization adducts of ethylene oxide with propylene oxide.

Examples of suitable anionic surface active agents are: alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the agricultural fungicidal compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition of the invention.

The above-mentioned carriers and various auxiliary agents may be used alone or in any desired combination, depending upon the type of preparation, the application and other factors.

In general, the fungicidal composition of the present invention may contain the compound of the invention in an amount of from 0.1 to 99% by weight, based upon the weight of the composition, although the precise amount of active ingredient in the composition will, naturally, depend upon the form of the composition, the manner in which it is to be applied and on whether or not the composition contains any other active ingredient.

For example, dusts may conveniently contain from 1 to 25% by weight of the compound of formula (I), the remainder being a solid carrier.

Wettable powders may conveniently contain, for example, from 25 to 90% by weight of the compound (I), the remainder being a solid carrier and a dispersing and wetting agent, if required, together with a protective colloidal agent, a thixotropic agent and an anti-foaming agent.

Granules may conveniently contain from 1 to 35% by weight of the compound of formula (I), a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the compound of formula (I) and from 5 to 20% by weight of an emulsifying agent, the remainder being a liquid carrier, together with, if required, a corrosion inhibitor.

The fungicidal compositions of the present invention, which are formulated into the various types of preparation described above, may be applied to a paddy or upland (dry) field in an amount of from 1 to 5000 g, more preferably from 10 to 1000 g, of the compound of formula (I) per 10 ares for pre- or post-emergence fungicidal activity; they may be applied by foliage spraying, soil drenching, spraying onto irrigation water or any other known method.

The fungicidal composition of the present invention, when employed for seed disinfection or coating, may effectively control soil-borne or seed infectious diseases by coating seeds in an amount of from 0.1 to 2%, preferably from 0.2 to 0.5%, by weight of the compound of formula (I), based on the weight of the seed.

The fungicidal composition of the present invention may additionally contain other fungicides in order to broaden the fungicidal spectrum and, in some cases, a synergistic effect may be observed. The composition may also contain plant growth regulators, herbicides, insecticides or fertilizers, as is well known in the art.

The fungicidal compositions of the present invention may be used together with control agents effective against rice blast, helminthosporium leaf spot, bacteriall leaf blight, rice stem borers, planthoppers and/or leafhoppers, to save the labour involved in separate applications. A combination of one or more of these additional control agents with the composition of the invention may be employed, depending upon the disease and/or the insect to be controlled and the form of the composition to be employed. We particularly prefer to employ the composition of the invention in the form of a dust, for the control of rice plant diseases and/or for soil treatment.

The invention is further illustrated by the following Examples, of which Examples 1 to 5 illustrate the preparation of compounds of the invention, Examples 6, 7 and 8 illustrate the preparation of compositions of the invention and Examples 9, 10 and 11 illustrate the biological activity of the compounds. In all of these Examples, all parts are by weight.

EXAMPLE 1

6-(3-Bromophenyl)-2-morpholinomethyl-3(2H)-pyridazinone (Compound No. 26)

To 20 ml of methanol were added 1 g of 6-(3-bromophenyl)-3(2H)-pyridazinone, 0.13 g of paraformaldehyde and 0.35 g of morpholine, and the resulting mixture was heated under reflux for 2 hours. The reaction mixture was then left to cool, after which the methanol was distilled off under reduced pressure. The residue was recrystallised from a 1:1 by volume mixture of ethyl acetate and hexane, to afford 0.76 g (yield 54%) of the desired Compound No. 26, melting at 110°–111° C.

Following the same procedure as described above but employing different pyridazinone derivatives and/or amines, the following compounds were also prepared:

6-(3,4-Dichlorophenyl)-2-N-isopropylaminomethyl-3(2H)-pyridazinone (Compound No. 10), melting at 197°–200° C.

6-(3,4-Dichlorophenyl)-2-(p-methylanilinomethyl)-3(2H)-pyridazinone (Compound No. 18), melting at 154°–155° C.

2-(p-Chloroanilinomethyl)-6-(3,4-dichlorophenyl)-3(2H)-pyridazinone (Compound No. 17), melting at 176°–177° C.

2-Cyclohexylaminomethyl-6-(3,4-dichlorophenyl)-3(2H)-pyridazinone (Compound No. 19), melting at 224°–226° C.

6-(3,4-Dichlorophenyl)-2-morpholinomethyl-3(2H)-pyridazinone (Compound No. 25), melting at 142°–144° C.

6-(3,4-Dichlorophenyl)-2-piperazinomethyl-3(2H)-pyridazinone (Compound No. 23), melting at 126°–127° C.

6-(3-Bromophenyl)-2-piperidinomethyl-3(2H)-pyridazinone (Compound No. 22), melting at 106° C.

6-(3-Bromophenyl)-2-morpholinomethyl-4,5-dihydro-3(2H)-pyridazinone (Compound No. 30), $n_D^{23} = 1.6078$.

6-(3,5-Dichloro-4-methylphenyl)-2-morpholinomethyl-4,5-dihydro-3(2H)-pyridazinone (Compound No. 29), melting at 175°–178° C.

6-(3,5-Dichloro-4-methylphenyl)-2-morpholinomethyl-3(2H)-pyridazinone (Compound No. 28), melting at 207°–209° C.

6-(3,5-Dichloro-4-methoxyphenyl)-2-morpholinomethyl-3(2H)-pyridazinone (Compound No. 27), melting at 164°–167° C.

EXAMPLE 2

1,4-Bis[6-(3,4-dichlorophenyl)-3(2H)-pyridazinon-2-yl-methyl]piperazine (Compound No. 34)

To 40 ml of methanol were added 1.0 g of 6-(3,4-dichlorophenyl)-3(2H)-pyridazinone, 0.2 g of paraformaldehyde and 0.25 g of piperazine, and the resulting mixture was heated under reflux for 2 hours. The mixture was then left to cool, after which insolubles were collected by filtration and dried, to give 1.1 g (yield 88%) of the desired Compound No. 34, melting at 271°–272° C.

Following the same procedure but employing 6-(3-bromophenyl)-3(2H)-pyridazinone, 1,4-bis[6-(3-bromophenyl)-3(2H)-pyridazinon-2-yl-methyl]piperazine (Compound No. 33), melting at 234°–236° C., was also prepared.

EXAMPLE 3

6-(3-Bromophenyl)-2-(N-butyl-N-methylaminomethyl)-3(2H)-pyridazinone (Compound No. 13)

4.5 g of 6-(3-bromophenyl)-2-chloromethyl-3(2H)-pyridazinone were heated with 10 ml of N-butyl-N-methylamine at 100°–110° C. on an oil bath for 2 hours. After the reaction mixture had been left to cool, the excess amine was distilled off under reduced pressure. To the resulting residue were added 100 ml of ethyl acetate and the mixture was left to stand overnight. The insolubles were removed by filtration and the filtrate was concentrated by evaporation under reduced pressure to a volume of about 20 ml. 100 ml of hexane and 20 ml of benzene were added to the concentrate and, after adding a small amount of active carbon, the mixture was filtered. The filtrate was concentrated by evaporation under reduced pressure and the residue was dried at 50° C. under a pressure of 13 Pa (0.1 mmHg) for 2 hours, to afford 5.0 g (yield 94%) of the desired Compound No. 13, in the form of a pale brown oil, $n_D^{23} = 1.5918$.

By following the procedure described above, but employing as the amine N,N-diallylamine, we also obtained 6-(3-bromophenyl)-2-(N,N-diallylaminomethyl)-3(2H)-pyridazinone (Compound No. 15), $n_D^{23} = 1.5905$.

EXAMPLE 4

6-(3-Bromophenyl)-2-hydroxymethyl-3(2H)-pyridazinone (Compound No. 1)

2.51 g of 6-(3-bromophenyl)-3(2H)-pyridazinone, 5 ml of a 37% formalin and 2 drops of concentrated hydrochloric acid were dissolved in 50 ml of methanol, and then the solution was heated under reflux for about 7 hours. The mixture was then left to stand overnight, after which it was filtered and the filtrate was concentrated by evaporation under reduced pressure. The resulting residue was extracted with a 1:1 by volume mixture of ethyl acetate and acetone. After distilling the solvent from the extract, there were obtained 1.13 g (yield 40%) of the desired Compound No. 1 in the form of a white solid melting at 228°–229° C.

Following the procedure described above but employing different pyridazinone derivatives, the following compounds were also prepared.

6-(3,5-Dichloro-4-methylphenyl)-2-hydroxymethyl-3(2H)-pyridazinone (Compound No. 2), melting at 243°–245° C.

6-(3,5-Dichloro-4-methylphenyl)-2-hydroxymethyl-4,5-dihydro-3(2H)-pyridazinone (Compound No. 3), melting at 198° C.

6-(3-Bromophenyl)-2-hydroxymethyl-4,5-dihydro-3(2H)-pyridazinone (Compound No. 4), melting at 133°–136° C.

EXAMPLE 5

6-(3-Bromophenyl)-2-chloromethyl-3(2H)-pyridazinone (Compound No. 5)

To 50 ml of dry benzene were added 2.51 g of 6-(3-bromophenyl)-3(2H)-pyridazinone, 0.45 g of paraformaldehyde and 1 ml of thionyl chloride, after which the mixture was heated under reflux for 1 hour. The mixture was then cooled and filtered, and the filtrate was evaporated to dryness under reduced pressure, to give 3.11 g of crude crystals of the desired Compound No. 5. These were recrystallised from a 4:1 by volume mixture of hexane and benzene, to give 2.0 g of pure Compound No. 5, in the form of white needles melting at 135°–137° C.

Following the procedure described above, but employing different pyridazinone derivatives, the following compounds were also prepared:

2-Chloromethyl-6-(3,4-dichlorophenyl)-3(2H)-pyridazinone (Compound No. 6), melting at 204°–205° C.

2-Chloromethyl-6-(3,5-dibromo-4-methylphenyl)-3(2H)-pyridazinone (Compound No. 7), melting at 201°–204° C.

2-Chloromethyl-6-(3,5-dichloro-4-methoxyphenyl)-3(2H)-pyridazinone (Compound No. 8), melting at 154°–157° C.

EXAMPLE 6

Dust 5 parts of Compound No. 2, 50 parts of talc and 45 parts of kaolin were uniformly mixed to form a dust.

EXAMPLE 7

Wettable Powder 50 parts of Compound No. 7, 29 parts of clay, 10 parts of diatomaceous earth, 5 parts of white carbon, 3 parts of sodium ligninsulphonate, 2 parts of "Newcol" 1106 (a trade name of Nihon Nyukazai K.K., Japan) and 1 part of polyvinyl alcohol were uniformly mixed in a mixer and then pulverized three times by a hammer mill to give a wettable powder.

EXAMPLE 8

Granules 70 parts of Compound No. 22 were finely pulverized, and 30 parts of clay were then added and mixed in a mixer to form a premix. 10 parts of this premix were uniformly mixed with 60 parts of clay and 30 parts of bentonite in a mixer. The mixture was kneaded with a suitable amount of water in a kneader, extruded through a screen having apertures of diameter 0.8 mm and dried in a draught drier at 50° C. The resulting product was formed into granules by means of a sifter.

The following Examples illustrate the use and activity of the compounds of the invention. In these Examples, the compound of the invention was employed in the form of a wettable powder, prepared as described in the Example 7, containing 50% by weight of the active compound.

For comparison, the tests described in these Examples were also carried out using two compounds outside of the scope of the present invention and within the scope of the disclosure of said Spanish Pat. No. 467,728, identified as follows:

Compound A: 6-(3,5-dichloro-4-methylphenyl)-2-methyl-3(2H)-pyridazinone;

Compound B: 6-(3-bromophenyl)-2-methyl-3(2H)-pyridazinone.

EXAMPLE 9

Preventive Effect Against Damping-Off on Cucumbers

The pathogenic fungus of damping-off (*Rhizoctonia solani*) was incubated on rice bran at 28° C. for 2 weeks and then homogeneously mixed with soil. The soil was placed in a pot having a diameter of 12 cm, and then 20 cucumber seeds of the variety Sagamihanpaku were sown thereon. The soil in the pot was then drenched with a test preparation containing one of the active compounds listed in the following Table 1 in a concentration of 250 ppm, at the rate of 3 liters of preparation per square meter of soil surface. The resulting pots were kept in a greedhouse at 25° C. for 2 weeks, after which the number of infected seedlings was determined. The results are summarised in Table 1.

A pot, similarly prepared, was kept as a control and not treated with any fungicidal preparation. The number of infected seedlings obtained from this pot is also reported in Table 1.

TABLE 1

| Compound | No. of infected seedlings | Compound No. | No. of infected seedlings |
|---|---|---|---|
| 1 | 2 | 22 | 2 |
| 2 | 2 | 26 | 5 |
| 5 | 3 | 33 | 7 |
| 8 | 3 | Untreated control | 56 |
| 10 | 7 | | |
| 19 | 8 | A | 40 |
| | | B | 36 |

EXAMPLE 10

Preventive Effect Against Sheath Blight on Rice Plants

Rice seedlings of the variety Koganenishiki at the 4–5 leaf stage were sprayed with a test preparation containing 30 ppm of one of the active compounds listed in Table 2 in a total amount of 50 ml per 3 pots. The host plants were left at room temperature for 24 hours, and then 4–5 oat grains, on which the pathogenic fungus of sheath blight (*Rhizoctonia solani*) had previously been cultured, were placed around the lower part of the stem of each rice plant. The plants were then placed in a greenhouse maintained at 25°–27° C. and, 10 days after introduction of the fungus, were examined for the degree of damage by determining the height of each diseased spot in centimeters. The results are shown in Table 2, in which the heights of the spots are reported as averages over each group of 3 pots.

As a control, the same experiment was repeated, except that the seedlings were not treated with any fungicidal compound. These results are also shown in Table 2.

TABLE 2

| Compound No. | Height of diseased spot (cm) | Compound No. | Height of diseased spot (cm) |
|---|---|---|---|
| 1 | 0.8 | 22 | 1.0 |
| 2 | 0.4 | 23 | 1.9 |
| 3 | 1.2 | 25 | 2.0 |
| 5 | 0.8 | 26 | 1.1 |
| 6 | 1.3 | 27 | 0.9 |
| 7 | 0.5 | 28 | 0.6 |
| 8 | 1.1 | 29 | 1.1 |
| 10 | 2.1 | 30 | 1.3 |
| 13 | 1.1 | 33 | 1.8 |
| 15 | 1.2 | 34 | 1.8 |
| 17 | 2.2 | Untreated control | 12.9 |
| 18 | 2.9 | | |
| 19 | 2.1 | A | 10.5 |
| | | B | 11.2 |

EXAMPLE 11

Curative Effect Against Sheath Blight of Rice Plants

Rice seedlings of the variety Koganenishiki at the 6-7 leaf stage were infected with sheath blight by placing around the lower part of the stem of each seedling 4-5 oat grains on which the pathogenic fungus of rice sheath blight (*Rhizoctonia solani*) had previously been cultured. The host plants were placed in a greenhouse maintained at 25°-27° C. and then, 3 days after introduction of the fungus (at which time the height of the diseased area was measured), the hosts plants were removed from the greenhouse and each was sprayed with a test preparation containing 100 ppm of one of the active compounds shown in the following Table 3, in a total amount of 50 ml of the preparation per 3 pots. The plants were air-dried and then again placed in the greenhouse at 25°-27° C. 10 days after the application, the degree of disease was investigated by determining the increase in the height of the diseased area (in centimeters) following application of the test preparation. These results obtained are shown in Table 3.

As a control, the experiment was repeated, except that the plants were not treated with any fungicidal compound. These results are also shown in Table 3.

TABLE 3

| Compound No. | Increase in height of diseased spot after application (cm) | Compound No. | Increase in height of diseased spot after application (cm) |
|---|---|---|---|
| 1 | 1.0 | 23 | 3.7 |
| 2 | 0.6 | 25 | 3.5 |
| 3 | 1.5 | 26 | 1.6 |
| 4 | 4.8 | 27 | 1.4 |
| 5 | 0.9 | 28 | 0.8 |
| 10 | 3.9 | 30 | 1.8 |
| 13 | 1.6 | 33 | 2.3 |
| 15 | 2.0 | 34 | 2.2 |
| 17 | 4.0 | Untreated | 15.1 |
| 18 | 4.0 | control | |
| 19 | 3.4 | A | 10.4 |
| 22 | 1.3 | B | 11.2 |

We claim:

1. Compounds of the formula (I):

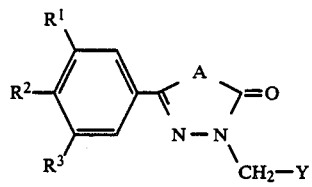

wherein:

A represents a group of formula —CH=CH— or —CH$_2$—CH$_2$;

R$^1$ represents a halogen atom;

R$^2$ represents a hydrogen atom, a hydroxy group, a halogen atom, an alkyl group having 1 to 4 carbon atoms or an alkoxy group having 1 to 4 carbon atoms;

R$^3$ represents a hydrogen atom or a halogen atom;

Y represents a hydroxy group; a halogen atom; an alkylamino group or a dialkylamino group having 1 to 8 carbon atoms in each alkyl group; an alkenylamino group or a dialkenylamino group having 3 or 4 carbon atoms in each alkenyl group; an anilino group in which the aromatic ring is unsubstituted or has one or two substituents selected from halogen atoms and alkyl groups having 1 to 4 carbon atoms; a 5, 6 or 7 member cycloalkylamino group; a 1-pyrrolidinyl group; a piperidino group; a morpholino group; a group of formula

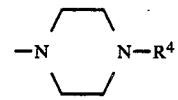

wherein R$^4$ represents an alkyl group having 1 to 4 carbon atoms or a phenyl group; or a group of formula

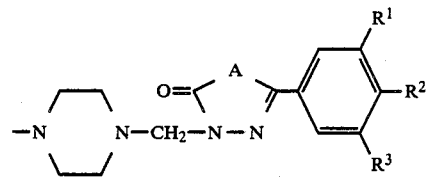

wherein A, R$^1$, R$^2$ and R$^3$ are as defined above.

2. Compounds as claimed in claim 1, wherein:

R$^1$ represents a halogen atom;

R$^2$ represents a hydrogen atom, a halogen atom or a C$_1$-C$_4$ alkyl group;

R$^3$ represents a hydrogen atom or a halogen atom; and

Y represents a halogen atom, a hydroxy group, an alkylamino group, a dialkylamino group, a dialkenylamino group, a 1-pyrrolidinyl group, a piperidino group or a morpholino group.

3. Compounds as claimed in claim 1, wherein:

R$^1$ and R$^3$ both represent halogen atoms;

R$^2$ represents a C$_1$-C$_4$ alkyl group or a halogen atom; and

Y represents a hydroxy group, a halogen atom, an alkylamino group, a dialkylamino group, a piperidino group or a morpholino group.

4. Compounds as claimed in claim 3, wherein A represents a group of formula —CH=CH—.

5. Compounds as claimed in claim 1, wherein:
$R^1$ represents a halogen atom;
$R^2$ represents a hydrogen atom or a halogen atom;
$R^3$ represents a hydrogen atom; and
Y represents a hydroxy group, a halogen atom, an alkylamino group, a dialkylamino group, a piperidino group or a morpholino group.

6. Compounds as claimed in claim 5, wherein A represents a group of formula —CH=CH—.

7. The compound claimed in claim 1 which is 6-(3-bromophenyl)-2-hydroxymethyl-3(2H)-pyridazinone.

8. The compound claimed in claim 1 which is 6-(3,5-dichloro-4-methylphenyl)-2-hydroxymethyl-3(2H)-pyridazinone.

9. The compound claimed in claim 1 which is 6-(3,4-dichlorophenyl)-2-hydroxymethyl-3(2H)-pyridazinone.

10. An agricultural fungicidal composition comprising a fungicidally effective amount of a fungicide in admixture with an agriculturally acceptable carrier or diluent, wherein said fungicide is at least one compound of the formula (I):

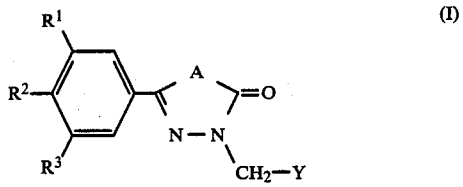
(I)

wherein:
A represents a group of formula —CH=CH— or —CH$_2$—CH$_2$—;
$R^1$ represents a halogen atom;
$R^2$ represents a hydrogen atom, a hydroxy group, a halogen atom, an alkyl group having 1 to 4 carbon atoms or an alkoxy group having 1 to 4 carbon atoms;
$R^3$ represents a hydrogen atom or a halogen atom;
Y represents a hydroxy group; a halogen atom; an alkylamino group or a dialkylamino group having 1 to 8 carbon atoms in each alkyl group; an alkenylamino group or a dialkenylamino group having 3 or 4 carbon atoms in each alkenyl group; an anilino group in which the aromatic ring is unsubstituted or has one or two substituents selected from halogen atoms and alkyl groups having 1 to 4 carbon atoms; a 5, 6 or 7 member cycloalkylamino group; a 1-pyrrolidinyl group; a piperidino group; a morpholino group; a group of formula

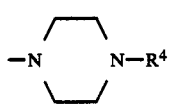

wherein $R^4$ represents an alkyl group having 1 to 4 carbon atoms or a phenyl group; or a group of formula

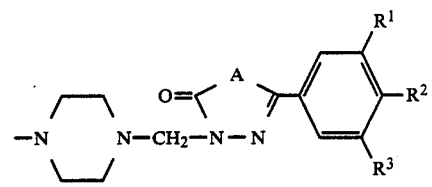

wherein A, $R^1$, $R^2$ and $R^3$ are as defined above.

11. A composition as claimed in claim 10, wherein:
$R^1$ represents a halogen atom;
$R^2$ represents a hydrogen atom, a halogen atom or a $C_1$-$C_4$ alkyl group;
$R^3$ represents a hydrogen atom or a halogen atom; and
Y represents a halogen atom, a hydroxy group, an alkylamino group, a dialkylamino group, a dialkenylamino group, a 1-pyrrolidinyl group, a piperidino group or a morpholino group.

12. A composition as claimed in claim 10, wherein:
$R^1$ and $R^3$ both represent halogen atoms;
$R^2$ represents a $C_1$-$C_4$ alkyl group or a halogen atom; and
Y represents a hydroxy group, a halogen atom, an alkylamino group, a dialkylamino group, a piperidino group or a morpholino group.

13. A composition as claimed in claim 12, wherein A represents a group of formula —CH=CH—.

14. A composition as claimed in claim 10, wherein:
$R^1$ represents a halogen atom;
$R^2$ represents a hydrogen atom or a halogen atom;
$R^3$ represents a hydrogen atom; and
Y represents a hydroxy group, a halogen atom, an alkylamino group, a dialkylamino group, a piperidino group or a morpholino group.

15. A composition as claimed in claim 14, wherein A represents a group of formula —CH=CH—.

16. A method of preventing or controlling fungal attack on seeds or growing plants by applying to the seeds or growing plants an effective amount of a fungicide, wherein the fungicide comprises at least one compound of the formula (I):

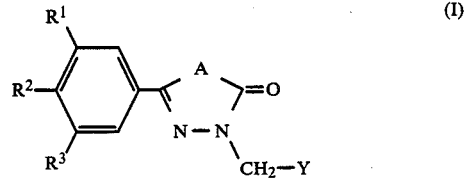
(I)

wherein:
A represents a group of formula —CH=CH— or —CH$_2$—CH$_2$—;
$R^1$ represents a halogen atom;
$R^2$ represents a hydrogen atom, a hydroxy group, a halogen atom, an alkyl group having 1 to 4 carbon atoms or an alkoxy group having 1 to 4 carbon atoms;
$R^3$ represents a hydrogen atom or a halogen atom;
Y represents a hydroxy group; a halogen atom; an alkylamino group or a dialkylamino group having 1 to 8 carbon atoms in each alkyl group; an alkenylamino group or a dialkenylamino group having 3 or 4 carbon atoms in each alkenyl group; an anilino group in which the aromatic ring is unsubstituted or has one or two substituents selected from halogen atoms and alkyl groups having 1 to 4 carbon atoms; a 5, 6 or 7 member cycloalkylamino group; a 1-pyrrolidinyl group; a piperidino group; a morpholino group; a group of formula

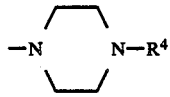

wherein $R^4$ represents an alkyl group having 1 to 4 carbon atoms or a phenyl group; or a group of formula

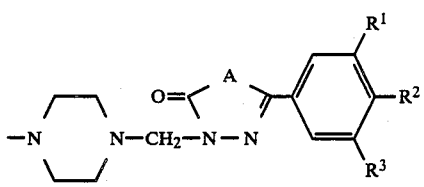

wherein A, $R^1$, $R^2$ and $R^3$ are as defined above.

17. A method as claimed in claim 16, wherein:
$R^1$ represents a halogen atom;
$R^2$ represents a hydrogen atom, a halogen atom or a $C_1$–$C_4$ alkyl group;
$R^3$ represents a hydrogen atom or a halogen atom; and
Y represents a halogen atom, a hydroxy group, an alkylamino group, a dialkylamino group, a dialkenylamino group, a 1-pyrrolidinyl group, a piperidino group or a morpholino group.

18. A method as claimed in claim 16, wherein:
$R^1$ and $R^3$ both represent halogen atoms;
$R^2$ represents a $C_1$–$C_4$ alkyl group or a halogen atom; and
Y represents a hydroxy group, a halogen atom, an alkylamino group, a dialkylamino group, a piperidino group or a morpholino group.

19. A method as claimed in claim 18, wherein A represents a group of formula —CH═CH—.

20. A method as claimed in claim 16, wherein:
$R^1$ represents a halogen atom;
$R^2$ represents a hydrogen atom or a halogen atom;
$R^3$ represents a hydrogen atom; and
Y represents a hydroxy group, a halogen atom, an alkylamino group, a dialkylamino group, a piperidino group or a morpholino group.

21. A method as claimed in claim 20, wherein A represents a group of formula —CH═CH—.

22. A method as claimed in claim 16, wherein said fungicide comprises 6-(3-bromophenyl)-2-hydroxymethyl-3(2H)-pyridazinone.

23. A method as claimed in claim 16, wherein said fungicide comprises 6-(3,5-dichloro-4-methylphenyl)-2-hydroxymethyl-3(2H)-pyridazinone.

24. A method as claimed in claim 16, wherein said fungicide comprises 6-(3,4-dichlorophenyl)-2-hydroxymethyl-3(2H)-pyridazinone.

* * * * *